US008241881B2

(12) United States Patent
Bradin

(10) Patent No.: US 8,241,881 B2
(45) Date of Patent: Aug. 14, 2012

(54) PRODUCTION OF GASOLINE FROM FERMENTABLE FEEDSTOCKS

(75) Inventor: David Bradin, Cary, NC (US)

(73) Assignee: CPS Biofuels, Inc., Raleigh, NC (US)

( * ) Notice: Subject to any disclaimer, the term of this patent is extended or adjusted under 35 U.S.C. 154(b) by 985 days.

(21) Appl. No.: 12/224,024

(22) PCT Filed: Feb. 14, 2007

(86) PCT No.: PCT/US2007/003746
§ 371 (c)(1),
(2), (4) Date: Aug. 14, 2008

(87) PCT Pub. No.: WO2007/095215
PCT Pub. Date: Aug. 23, 2007

(65) Prior Publication Data
US 2010/0159553 A1    Jun. 24, 2010

Related U.S. Application Data

(60) Provisional application No. 60/773,279, filed on Feb. 14, 2006.

(51) Int. Cl.
*C12P 5/02*  (2006.01)
*C12P 1/04*  (2006.01)
*C12P 1/02*  (2006.01)
*C12N 1/20*  (2006.01)

(52) U.S. Cl. ..... 435/167; 435/170; 435/171; 435/252.3; 435/320.1

(58) Field of Classification Search .................. None
See application file for complete search history.

(56) References Cited

U.S. PATENT DOCUMENTS
4,278,505 A * 7/1981 Danulat et al. .................. 203/59

OTHER PUBLICATIONS

Zhu et al. Biotechnol Prog. Mar.-Apr. 2003;19(2):365-72.*
de Carvalho Lima et al. J Ind Microbiol Biotechnol. Sep. 2002;29(3):124-8.*
Sun et al. Bioresour Technol. May 2002;83(1):1-11.*
Galitsky et al. "Energy Efficiency Improvement and Cost Saving Opportunities for the Corn Wet Milling Industry". Jul. 2003.*
Levy et al. J. Electrochem. Soc., vol. 131(4), pp. 773-777 (1984).*
Schumacher et al. Water Sci Technol. 2003;47(11):195-202.*

* cited by examiner

*Primary Examiner* — Christian Fronda
(74) *Attorney, Agent, or Firm* — Guerry L. Grune; ePatentmanager.com

(57) ABSTRACT

Compositions and methods for forming hexane, and, optionally, gasoline and/or components of a gasoline composition, from fermentable sugars are disclosed. The sugars are fermented using a bacteria or yeast that predominantly forms butyric acid. The butyric acid is subjected to Kolbe or photo-Kolbe electrolysis to form hexane. The hexane can be subjected to catalytic, reforming and/or isomerization steps to form higher octane products, which are or can be included in gasoline compositions. In one aspect, the fermentable sugars are derived from lignocellulosic materials such as wood products, switchgrass, or agricultural wastes. These materials are delignified to form lignin, cellulose and hemicellulose. The cellulose and hemicellulose are depolymerized to form glycose and xylose, either or both of which can be fermented by the bacteria. The lignin can be used to generate heat energy and/or electric energy for use in one or more process steps, such as the fermentation, product isolation, Kolbe electrolysis, catalytic reforming and/or isomerization steps. Alternatively, the lignin can be converted to synthesis gas, which can then be subjected to Fischer-Tropsch synthesis, or converted to methanol and/or ethanol. Thus, the methods described herein can convert biomass to a fuel composition or fuel additive, which can be used in a conventional gasoline engine, unlike traditional fuels such as ethanol or biodiesel.

13 Claims, No Drawings

US 8,241,881 B2

PRODUCTION OF GASOLINE FROM FERMENTABLE FEEDSTOCKS

This application claims priority to U.S. Provisional Application Ser. No. 60/773,279, filed Feb. 14, 2006, the contents of which are hereby incorporated by reference in its entirety.

FIELD OF THE INVENTION

The present invention relates to methods for producing a fuel product that can burn in a gasoline engine, from feedstocks containing, or which can be coverted into, glucose, fructose, sucrose, and/or xylose. In particular, the invention relates to a method to ferment sugars to butyric acid, convert the butyric acid to hexane, and, optionally, subject the hexane to catalytic reforming to form hydrocarbons that burn in gasoline engines.

BACKGROUND OF THE INVENTION

There are numerous efforts underway to generate renewable fuels from biomass ("biofuels"). One approach is to generate biodiesel fuel (predominantly fatty acid ethyl or methyl esters) from triglycerides. Another approach is to use the glycerol to form glycerol ethers, which can be added to biodiesel and/or diesel fuel. Still another approach is to convert cellulosic or starchy material to fermentable sugars, ferment the sugars to form alcohol, and add the alcohol to gasoline, such as E85 (an 85/15 ethanol/gasoline blend).

Each of these approaches is associated with certain limitations. To date, biomass has not been converted to hydrocarbons in the gasoline range, only biodiesel fuel, glycerol ethers, ethanol, and butanol. Since the majority of cars run on gasoline, this is a major limitation. Ethanol works fairly well as a gasoline additive, but the energy output in miles per gallon ("MPG") is far lower for gasoline/alcohol blends than for gasoline.

In addition, yeasts have a limited ability to use sugars other than glucose. Glucose is only one of the sugars available from starch hydrolysis or from the depolymerization of cellulose or hemicellulose. Agricultural wastes such as corn stover and rice straw, and biomass crops such as switch grass or poplar trees, and even waste newspaper can all be converted into ethanol. However, a major limitation of these processes is that these feedstocks also include large amounts of other sugars, such as xylose, which yeast cannot easily metabolize.

In order to maximize the yield from biomass, it would be advantageous to provide fermentation processes that use sugars other than glucose. In order to facilitate adoption of alternative fuels, it would be advantageous to provide alternative fuels and fuel additives that can be used in the world's existing energy infrastructure. The present invention provides such processes and alternative fuels and fuel additives.

SUMMARY OF THE INVENTION

In one aspect, the present invention relates to a process for converting biomass to hexane, and, optionally, to hexane isomers, and using the hexane isomers as an alternative fuel or fuel additive.

Representative sugars that can be fermented include glucose, sucrose, fructose, and xylose. Starting from sugar, the process for producing hexane comprises two main steps. The first step is the fermentation of sugar to butyric acid or (butyrate ion), and the second step is the Kolbe electrolysis of butyric acid or butyrate ions to form hexane. In one embodiment, the process further involves the conversion of hexane to hexane isomers and/or aromatics, for example, by catalytic reforming and/or isomerization.

The sugars can be derived from carbohydrate hydrolysis, from cellulose and/or hemicellulose depolymerization, or other means for producing sugars. As such, the sugars can be derived from virtually any cellulosic or starchy material. Examples include sugar cane bagasse, wood pulp, sawdust and wood chips, recycled paper, switch grass, corn, corn husks and other plant materials. Many of these materials are lignocellulosic materials, which include a combination of lignin, cellulose and hemicellulose. Because xylose is inefficiently converted to ethanol, this process can be complementary to ethanol production. Xylose is a preferred feedstock.

There are several bacteria known to ferment monosaccharides to butyric acid, any of which can be used. The fermentation is typically performed under anaerobic conditions, since the bacteria/yeast are anaerobic in nature. One way to ensure that no aerobic fermentation occurs, such as that which would produce ethanol, is to bubble sulfur dioxide into the fermentation media. Examples of butyrate-producing bacteria include *Clostridium tyrobutyricum, Clostridium butyricum, Clostridium kluyveri, Clostridium pasteurianum, Fusobacterium nucleatum, Butyrivibrio fibrisolvens,* and *Eubacterium limosum*. Many of these also produce by-products, such as acetic acid, which lowers the overall yield. For this reason, it can be preferred to use bacteria which have been bred and/or genetically-modified to produce less or no acetic acid or other by-products than the wild-type bacteria.

Butyric acid, when subjected to Kolbe electrolysis, or to photo-Kolbe conditions, forms hexane and hydrogen, with minor amounts of propane. The hexane is immiscible with the fermentation broth, and is easily separated. The hexane can be used as a solvent, as a fuel or fuel additive, or, optionally, can be subjected to catalytic reforming and/or isomerization conditions to form hydrocarbons in the gasoline range, which can be used directly in gasoline engines, or as a high-octane fuel additive.

Kolbe electrolysis conditions are known in the art, and include platinum electrodes, sonoemulsion with various electrodes such as boron-doped chemical vapor deposition diamond electrodes (Pure and Applied Chemistry, 73 (12):1947-1955 (2001), polymer electrodes, and the like. Kolbe electrolysis typically works with the carboxylate anion rather than the acid itself. In one embodiment, the Kolbe electrolysis is performed on the fermentation broth. This permits the hexane product to separate from the fermentation broth and be separated by decantation, distillation or other means. Thus, a continuous or semi-continuous process can be envisioned, where sugar is added to the system while the hexane is formed, and removed, for example, using evaporative distillation, decantation, and the like.

In another embodiment, the fermentation is completed, and the butyric acid/butyrate ions optionally isolated, before the Kolbe electrolysis is performed. Butyric acid can be removed from the fermentation broth, for example, by continuous extraction with a solvent such as hexane, and butyrate ions formed by extraction of the hexane with a basic solvent.

If the Kolbe electrolysis or photo-Kolbe electrolysis occurs after the fermentation takes place, the bacteria/yeast can be collected, for example, by decantation or filtration of the fermentation media, and a new batch of water containing fermentable sugars can be combined with the bacteria/yeast. The fermentation media including the butyric acid can be subjected to Kolbe electrolysis or photo-Kolbe electrolysis, and the resulting products (hexane, propane, hydrogen and carbon dioxide) easily separate from the aqueous fermentation solution and can be easily isolated, for example, by collecting the gases (propane, carbon dioxide and hydrogen) and separating them into their components, and by decanting or distilling the hexane. The aqueous solution can then be recycled to the fermenter, if desired, or otherwise disposed of.

Lignocellulosic materials include cellulose, hemicellulose, and a large amount of lignin. Cellulose is a glucose polymer, and hemicellulose is a glucose copolymer. These polymeric materials can be degraded, for example, using enzymatic degradation, to form fermentable monosaccharides. These saccharides primarily include glucose and xylose, either or both of which can be used to hexane (and hexane isomers and/or aromatics). Lignin can be burned, and the energy from burning the lignin can fuel many of the operations, such as distillation, catalytic reforming, and isomerization, used in the processes described herein. Electricity can be generated from burning the lignin, and this electricity can power the Kolbe electrolysis described herein. The lignin can also be converted to syngas, and subjected to Fischer-Tropsch synthesis. The Fischer-Tropsch synthesis can be used to produce additional hydrocarbons suitable for use as feedstocks for making diesel or gasoline, as is known in the art.

In one embodiment, lignocellulosic materials are used to produce lignin, hemicellulose, and cellulose as separate fractions. There are several known methods for separating cellulose and hemicellulose from lignin, such as those used in the pulp and paper industry. Any of these can be used. The cellulose can be depolymerized to form glucose, and the hemicellulose can be depolymerized to form xylose. The glucose can be used in the to process disclosed herein, or, alternatively, fermented to form ethanol, and the xylose can be used in the process described herein to form hexane, hexane isomers, or aromatics. The lignin can be converted to syngas, and the syngas to other products, such as gasoline, diesel, or jet fuel.

Some species of algae are ideally suited to biodiesel production due to their high oil content (some well over 50% oil), and extremely fast growth rates. The carbon dioxide formed during the initial fermentation of sugars to butyric acid, and during the subsequent Kolbe electrolysis, can be used to feed algae, where the algae generates triglycerides. Typically, a solvent such as hexane is used to extract the triglycerides from the algae. The hexane for this extraction can be derived from the process described herein. Thus, the process described herein for producing hexane (and, optionally, hexane isomers and/or aromatics) is complementary to the process for producing triglycerides from algae, in that the feedstock for the growing algae and the extractant for the thus-formed triglycerides both can be derived from the process.

The process described herein also provides a source of hydrogen, derived from both the fermentation step and the Kolbe electrolysis step. The hydrogen produced by the process can be used in fuel cells, in a Fischer-Tropsch reactor, as a fuel, or any other appropriate use for hydrogen. Gasoline, jet fuel, and diesel fuel derived from Fischer-Trospch synthesis are all well known to those of skill in the art. The carbon dioxide produced by the process can be trapped by algae, and used to produce triglycerides (which can be extracted using the hexane and/or hexane isomers produced by the process described herein). The triglycerides can be used, for example, to produce biodiesel fuel. Thus, from lignocellulosic materials, products useful in gasoline, jet, and diesel engines can be produced, with much of the carbon dioxide that is formed being sequestered in the form of a fuel product.

In one embodiment, one or more fatty acids are added to the reaction mixture during the Kolbe electrolysis or photo-Kolbe electrolysis step. These fatty acids will form radicals of the alkyl group to which the carboxylic acid group is attached. These radicals can react with any propyl radicals formed by the decarboxylation of butyric acid. In this case, the reaction products will include hexane, a mixed-Kolbe electrolysis product that is a three-carbon extension of the decarboxylated fatty acid radical, and a dimer of the fatty acid radical, as well as propane, carbon dioxide and hydrogen. In this embodiment, the gaseous products (propane, carbon dioxide and hydrogen) are easily separated, and the hexane can be distilled from the other two products. The reaction product including a three-carbon to extension of the fatty acid radical(s) can be used as diesel fuel, and the dimers of the fatty acid radical(s) can be used as motor oil, or hydrocracked or otherwise converted to diesel fuel or gasoline.

There are numerous advantages of this process, over conventional processes for converting fermentable materials to ethanol. Whereas gasoline/alcohol blends provide fewer miles per gallon than gasoline, the instant process provides hydrocarbons in the gasoline range, from the same starting materials as those used to form ethanol, but which have higher energy per unit volume. However, because there is a loss of carbon dioxide when the butyric acid is converted to hexane, the overall yields may be lower than when ethanol is produced.

DETAILED DESCRIPTION OF THE INVENTION

The present invention subjects sugars, such as those derived from biomass, waste wood pulp, wood chips, paper products, and other sources of fermentable sugars, to anaerobic fermentation conditions that favor butyric acid and/or isobutyric acid synthesis. Kolbe or photo-Kolbe electrolysis forms hexane(s), and catalytic reformation and/or isomerization converts the hexane to hexane isomers and/or aromatics, which can be used directly as gasoline, or as components of a gasoline composition.

Using the methods described herein, with the abundant sources of fermentable sugars, one can synthesize enough gasoline to replace a substantial portion of the amount consumed that is presently derived from crude oil. The methods for converting fermentable sugars to hexane, gasoline, and/or components of gasoline are described in more detail below.

I. Sources of Fermentable Sugars

There are many sources of fermentable sugars. These include corn syrup, steepwater, sugar derived from beets and/or sugar cane, cellulosic materials and lignocellulosic materials. The lignocellulose materials include switchgrass, softwood pulps, hardwood pulps and non-wood plant pulps, for example, kenaf, flax, bagasse and rice plant pulps.

Cellulose, a glucose polymer, can be converted to glucose by using cellulose enzymes. Waste paper and delignified wood pulp can be used as cellulosic feedstocks for this conversion.

Lignocellosic materials, on the other hand, must first be delignified. Delignification methods are well known to those of skill in the art, and include the use of various enzymes, such as xylanases, and oxidizing agents such as ozone, oxygen, hydrogen peroxide, chlorine, and chlorine dioxide. Wood pulp that has been subjected to delignification is often referred to as "chemical pulp." Representative chemical pulps include Kraft pulps and soda pulps, which can be hardwood Kraft pulps or softwood Kraft pulps. The pulp is optionally digested, or digested and oxygen-bleached, before the enzyme treatment.

Representative enzymes for enzymatic delignification, and for hemicellulose depolymerization, include hemicellulases, such as xylanase, manganese peroxidase and laccase mediator systems. Numerous hemicellulases are commercially, any of which can be used. For example, hemicullulase-containing agents available in trade under the trademark of CALTAZYME, made by CLARIANT CO., ECOPULP, made by RHOM ENZYME FINLAND OY, or SUMIZYME, made by SHINNIHON CHEMICAL CO., and xylanase produced by microorganisms in genus *Tricoderma*, genus *Termomyces*, genus *Aureobasidium*, genus *Streptomyces*, genus *Aspergillus*, genus *Clostridium*, genus *Bacillus*, genus *Dermatoga*, genus *Thermoascus*, genus *Cardoceram* and genus *Thermomonospora*, can be employed. Such hemicellulase contributes to enhancing the bleaching efficiency in the enzyme treatment step by decomposing and removing the hemicellulose in the chemical pulp.

To form xylose from a chemical pulp, the pulp can be subjected to an enzyme treatment using hemicellulase, and after a permeation treatment using the separation membrane is completed, the resultant non-permeated fraction can be collected. In the non-permeated fraction, the xylooligosaccharide-lignin complex can be concentrated, and separated from the non-permeated fraction. A xylooligosaccharide can be isolated from a xylooligosaccharide-lignin complex by adjusting the pH value of the non-permeated fraction to 2 to 4 and heating the complex for an appropriate amount of time at an appropriate temperature. During the heating procedure, the xylooligosaccharide complex is converted into a mixture of mono- to decamers of xylose. The di- to decamers of xylose is recovered together with the remaining xylooligosaccharide from the heated non-permeated fraction. Further processing, for example, with hemicellulases, converts the di- to decamers of xylose to xylose, as is known in the art. The reaction mixture delivered from the enzyme treatment system can be filtered to recover the enzyme-treated pulp, and a filtrate containing various saccharides can be collected. In some processes, when a hardwood Kraft pulp is used, the filtrate contains substantially no glucose or arabinose, and xylose is obtained as close to 100% of the saccharides in the filtrate.

II. Selection of Bacteria for Fermenting the Sugars to Butyric Acid

Butyrate is produced as end product of a fermentation process solely performed by obligate anaerobic bacteria. Examples of butyrate producing species include *Clostridium tyrobutyricum, Clostridium butyricum, Clostridium kluyveri, Clostridium pasteurianum, Fusobacterium nucleatum, Butyrivibrio fibrisolvens*, and *Eubacterium limosum*.

The pathway starts with the glycolytic cleavage of glucose to two molecules of pyruvate, as happens in most organisms. Pyruvate is then oxidized into acetyl coenzyme A using a unique mechanism that involves an enzyme system called pyruvate-ferredoxin oxidoreductase. Two molecules of carbon dioxide ($CO_2$) and two molecules of elemental hydrogen ($H_2$) are formed in the process and exit the cell.

Then, acetyl coenzyme A converts into acetoacetyl coenzyme A; the responsible enzyme is acetyl-CoA-acetyl transferase. Acetoacetyl coenzyme A converts into β-hydroxybutyryl CoA, and the responsible enzyme for this conversion is β-hydroxybutyryl-CoA dehydrogenase. β-hydroxybutyryl CoA converts into crotonyl CoA, and the responsible enzyme is crotonase. Crotonyl CoA converts into butyryl CoA ($CH_3CH_2CH_2C{=}O$—CoA), and the responsible enzyme is butyryl CoA dehydrogenase.

A phosphate group replaces CoA to form butyryl phosphate; responsible enzyme: phosphobutyrylase.

The phosphate group joins ADP to form ATP and butyrate; responsible enzyme: butyrate kinase.

ATP is produced, as can be seen, in the last step of the fermentation. 3 ATPs are produced for each glucose molecule, a relatively high yield. The balanced equation for this fermentation is:

$$C_6H_{12}O_6 \rightarrow C_4H_8O_2 + 2CO_2 2H_2$$

There are several known strains of *Clostridium* bacteria which, under anaerobic conditions, convert glucose, fructose, and xylose to butyric acid, among other fermentation products. Acetic acid is one of the other products that are commonly produced.

Many clostridia are capable of forming butyric acid as an end product of their metabolism, which has a distinct rancid aroma and is often associated with this genus. Four nutritional groups of clostridia have been established based upon their preferred growth substrates: saccharolytic, proteolytic, saccharolytic and proteolytic and the so-called specialists. Saccharolytic clostridia use carbohydrates such as xylose, mannitol, glucose, fructose, lactose, or raffinose as their primary source of carbon and energy. Some saccharolytic species specialize in degrading polymers such as cellulose, chitin and pectin through the secretion of exoenzymes into the environment. Proteolytic species excrete proteases into the environment that degrade proteins to peptides and amino acids that are then transported inside the cell. The third group of clostridia can utilize both proteolytic and saccharolytic pathways for growth. The specialists are those clostridia that are restricted to degradation of just one or a few compounds. For example, *Clostridium acidiurici* grows on purines such as adenine or uridine, but not on sugars or amino acids, whereas *Clostridium cochlearium* can only use glutamate, glutamine, and histidine for growth. As a group, however, clostridia are capable of attacking a wide variety of substrates and play an important role in the degradation of organic compounds in many anaerobic environments

*Clostridium tyrobutyricum* is an anaerobe producing butyric acid, acetic acid, hydrogen and carbon dioxide. Researchers have engineered *Clostridium* bacteria which include mutations in various genes necessary to produce acetic acid, to maximize the yields of butyric acid. These genes include ack and pta, encoding enzymes AK and PTA, which are each involved in the acetate formation pathway. Gene knockout experiments were carried out in over-producing strains, and the results were published (*Biotechnol. Bioeng.* 90:154-166 (2005).

One example of a suitable genetically modified *Clostridium tyrobutyricum* is *Clostridium tyrobutyricum* ATCC 25755, an acidogenic bacterium, producing butyric acid, acetic acid, carbon dioxide and hydrogen as its main fermentation products. In these bacteria, genes in the acetic acid formation pathway in *C. tyrobutyricum* were disrupted, in order to enhance the production of butyrate and hydrogen. http://www.ct.ornl.gov/symposium/index_files/5abstracts/5_11.htm These researchers produced two mutants, phosphotransacetylase gene (pta) deleted mutant (PPTA-Em) and higher hydrogen-producing mutant (HydEm), which are capable of producing butyric acid and hydrogen from glucose and xylose, both of which are formed from lignocellulosic materials. Of these two, PPTA-Em produced a higher concentration (>50 g/L) of butyric acid with a higher yield (>50%) than those from the wild type *Clostridium tyrobutyricum*. Xylose is a preferred feedstock for these bacteria, producing significantly higher yields of butyric acid than glucose.

The ability to effectively minimize or shut off acetic acid production is an important component to the present invention. That is, butyric acid can be converted, via Kolbe electrolysis, to a mixture including mostly hexane, and a minor amount of propane. A mixture containing both acetic acid and butyric acid is converted, via Kolbe electrolysis, to a mixture of methane, ethane, propane, butane and hexane. While the methane, ethane, propane and butane (collectively, natural gas) are readily separated from the hexane, the yield of hexane is reduced. Accordingly, bacteria which predominantly form butyric acid (or butyrate) over acetic acid (or acetate) are preferred. Ideally, the bacteria form butyric acid predominantly over acetic acid (i.e., a ratio of butyric acid/acetic acid of at least 2:1, preferably 3:1, more preferably 4:1 or more).

III. Fermentation Conditions.

Ideally, the bacteria are restrained in immobilized cell bioreactors, such as fibrous-bed bioreactors (FBBs), to carry out the fermentation. However, any type of fermenter can be used. The use of immobilized cell bioreactors helps re-use the bacteria. However, in those embodiments where Kolbe electrolysis and/or photo-Kolbe electrolysis is carried out on the fermentation media, the hexane will be easily removed from the reaction media, so immobilization of the bacteria will not be a problem in this embodiment. When the bacteria are not immobilized, they can be isolated, for example, using centrifugal bacterial reclamation.

Continuous decantation, evaporative removal, or extraction of the hexane allows the fermentation medium to be continuously sterilized and minimizes water use. The non-stop nature of the fermentation process allows substrate concentrations to be constantly kept at optimal levels and therefore fermentation efficiency is maximized.

Improved varieties of bacteria, produced through clonal selection techniques, can raise the tolerance levels of the bacteria to butyric acid concentrations, which will also improve efficiency. That said, currently known *Clostridium* variants can produce up to 50 g/liter of butyric acid, which is a fairly high tolerance level.

In some embodiments, it may be desirable to remove the butyric acid from the fermentation broth prior to fermentation. Butyric acid can be removed from the fermentation broth, for example, by continuous extraction with a solvent such as hexane, and butyrate ions formed by extraction of the hexane with a basic solvent. Such a dual extraction is described, for example, in Sanderson et al., "Liquid fuel production from biomass," Sun II; Proceedings of the Silver Jubilee Congress, Atlanta, Ga., May 28-Jun. 1, 1979, Volume 1. (A80-33401 13-44) p. 63-67, Elmsford, N.Y., Pergamon Press, Inc., 1979, the contents of which are hereby incorporated by reference. Although Sandersen described the fermentation of algae to organic acids, the same techniques can be applied to the fermentation of sugars. Additionally, the use of algae to produce triglycerides and/or to sequester carbon dioxide produced during the fermentation and/ Kolbe electrolysis steps is described herein. The fermentation described by Sandersen can be used to provide additional acids from the sequestered carbon dioxide, optionally after a desired amount of triglycerides are obtained.

IV. Kolbe Electrolysis and Photo-Kolbe Electrolysis

The butyric acid and/or isobutyric acid formed during the fermentation can be converted to hexane via Kolbe electrolysis, photo-Kolbe electrolysis, or enzymatic decarboxylation. Suitable enzymes and reaction conditions for enzymatic hydrolysis are known in the art (see, for example, http://arginine.chem.cornell.edu/Publications/Abstracts/Abs149.html). Decarboxylation reactions are widespread in biochemical pathways. The main feature of a decarboxylase is its ability to stabilize the developing carbanion, most often through delocalization of the negative charge. Three suitable enzymes are S-adenosylmethionine decarboxylase, phosphoribosyl carboxyaminoimidazole mutase and orotidine-5'-monophosphate decarboxylase. In one embodiment, these enzymes are present in the fermenter, to react with the butyric acid and isobutyric acid as they are formed.

Kolbe electrolysis is an anodic oxidation process of a carboxylate anion. A radical is formed, which then decarboxylates. The resulting radical combines with another to form a dimer. For example, acetic acid will lose a mole of carbon dioxide to produce a methyl radical, two of which will combine to form ethane. The efficiency of Kolbe electrolysis is sensitive to water. It can therefore be preferred to run the reaction in (almost) water free conditions.

In one embodiment, the Kolbe electrolysis is performed in an ionic liquid, which can optionally be present in the fermenter. In another embodiment, anion exchange membranes are used as solid polymer electrolytes (http://www.pca-gmbh.com/appli/spe.htm). One example of a suitable electrode system is a monel cathode and platinum sheet or platinum gauze anode.

In Kolbe electrolysis, there are some competing reactions, such as an elimination reaction which would convert butyric acid to propylene, carbon dioxide and hydrogen. Low temperatures (i.e., 30-40° C.) and high flow rates over the electrodes tend to favor paraffin formation, rather than elimination.

In one aspect, the electricity used to perform the Kolbe electrolysis is derived from lignin and/or any propane derived from the Kolbe electrolysis of a previous batch of butyric and/or isobutyric acid. In this aspect, the lignin from the lignocellulosic materials can provide the electric power for the Kolbe electrolysis, and the sugars derived from the cellulose and hemicellulose can be converted to the butyric and/or isobutyric acids to be converted, via Kolbe electrolysis, to hexane. Thus, the process can use each component of the lignocellulosic materials, and the waste stream is simply water and carbon dioxide.

The photo-Kolbe reaction is described, for example, in U.S. Pat. No. 4,303,486, the contents of which are hereby incorporated by reference in their entirety. Briefly, butyric acid is decarboxylated by irradiating a suspension of a suitable photo-Kolbe catalyst in a solution containing the acid, such as the fermentation media. Appropriate catalysts include, for example, an n-type $TiO_2$ powder, in an aqueous solution containing the butyric acid. The suspension is irradiated and decarboxylation occurs resulting in the formation of hexane and carbon dioxide as the primary reaction products. The reaction occurs at ambient temperature.

V. Isolation of Hexane

Hexane has a relatively low boiling point, and can be removed from the fermentation media by distillation at atmospheric pressure or under vacuum, if desired. However, since the hexane is insoluble in, and floats to the top of, the fermentation media, it may be desired to simply decant it from the fermentation media. If the reaction is run as a continuous process, as hexane is removed, additional fermentable sugars can be added to the fermenter. Hexane can similarly be removed from a Kolbe electrolysis reactor, if the Kolbe electrolysis is run separately from the fermentation, for example, by decantation or distillation, depending on the nature of the solvents present in the Kolbe electrolysis reactor.

VI. Catalytic Reforming and/or Isomerization of the Hexane

Gasoline typically includes hydrocarbons in the $C_{5-12}$ range, and the hydrocarbons are predominantly in the $C_{6-8}$ range. The hydrocarbons can include aromatics, cycloaliphatics, and isoparaffins, all of which have higher octane values than linear hydrocarbons like hexane. For this reason, it can be advantageous to subject the hexane to catalytic reforming and/or isomerization conditions, to provide hydrocarbons with higher octane values than hexane. Hydrogenation, hydrofinishing and hydrotreatment steps can also be performed.

Hexane has a relatively low octane value (approximately 24 octane), and high octane gasoline is required for modern gasoline engines. The hexane produced during the Kolbe electrolysis stage can be subjected to catalytic reforming and/or catalytic isomerization to upgrade the octane values. These processes are well known to those of skill in the art.

Isomerization can be used to rearrange the structure of the hexane into branched-chain paraffins. Reforming conditions can be used to convert the hexane to aromatic compounds. Although hexane can be upgraded into aromatics through hydrocyclization, the conversion of hexane to aromatics creates higher density species and increases gas yields, with both effects leading to a reduction in liquid volume yields. Moreover, the health concerns related to benzene are likely to generate overall restrictions on benzene and possibly aromatics as well, which some view as precursors for benzene tail pipe emissions. Therefore, it is preferred to convert the hexane to $C_6$ isoparaffins using an isomerization unit.

Combination processes using isomerization and reforming to convert naphtha range feedstocks are well known. For example, U.S. Pat. No. 4,457,832, the contents of which are hereby incorporated by reference, uses reforming and isomerization in combination to upgrade a naphtha feedstock by first reforming the feedstock, separating a $C_{5-6}$ paraffin fraction from the reformate product, isomerizing the $C_{5-6}$ fraction to upgrade the octane number of these components and recovering a $C_{5-6}$ isomerate liquid which may be blended with the reformate product. U.S. Pat. Nos. 4,181,599 and 3,761,392, the contents of each of which are hereby incorporated by reference, show a combination isomerization-reforming process where a full range naphtha boiling feedstock enters a first distillation zone which splits the feedstock into a lighter fraction which enters an isomerization zone and a heavier fraction that is charged as feed to a reforming zone. In both the '392 and '599 patents, reformate from one or more reforming zones undergoes additional separation and conversion, the separation including possible aromatics recovery, which results in additional C5-C6 hydrocarbons being charged to the isomerization zone.

The effluent from a reforming zone will contain a portion of hydrogen which may be used in the isomerization zone. Therefore combining the effluents to separate a stream containing hydrogen for recycle to the isomerization zone is desirable. Isomerized products are separate in a common vessel with the reforming zone products. Portions of the streams from the integrated separation may be recycled, may be used in gasoline blending or may be further processed.

Isomerization processes are generally carried out at a temperature between 200° F. and 700° F., preferably 300° F. to 550° F., with a liquid hourly space velocity between 0.1 and 2, preferably between 0.25 and 0.50. The hydrogen content is adjusted such that the hydrogen to hydrocarbon mole ratio is between 1:1 and 5:1. Catalysts useful for isomerization are generally bifunctional catalysts comprising a hydrogenation component (preferably selected from the Group VIII metals of the Periodic Table of the Elements, and more preferably selected from the group consisting of nickel, platinum, palladium and mixtures thereof) and an acid component. Examples of an acid component useful in the preferred isomerization catalyst include a crystalline zeolite, a halogenated alumina component, or a silica-alumina component. Such paraffin isomerization catalysts are well known in the art.

VII. Formation of a Fuel Additive or Fuel Product

The products of the catalytic reformation and/or isomerization can be used alone, either as a fuel or fuel additive, or can be combined with other desired gasoline components to form a gasoline composition. The gasoline composition can include various additives, such as lubricants, emulsifiers, wetting agents, densifiers, fluid-loss additives, corrosion inhibitors, oxidation inhibitors, friction modifiers, demulsifiers, anti-wear agents, anti-foaming agents, detergents, rust inhibitors and the like. Other hydrocarbons, such as those described in U.S. Pat. Nos. 5,096,883 and/or 5,189,012, may be blended with the fuel, provided that the final blend has the necessary octane values, pour, cloud and freeze points, kinematic viscosity, flash point, and toxicity properties.

Detergent additives are typically used in the concentration range of 50 ppm to 300 ppm. Examples of detergents and metal rust inhibitors include the metal salts of sulfonic acids, alkylphenols, sulfurized alkylphenols, alkyl salicylates, naphthenates and other oil soluble mono and dicarboxylic acids such as tetrapropyl succinic anhydride. Neutral or highly basic metal salts such as highly basic alkaline earth metal sulfonates (especially calcium and magnesium salts) are frequently used as such detergents. Also useful is nonylphenol sulfide. Similar materials made by reacting an alkylphenol with commercial sulfur dichloride. Suitable alkylphenol sulfides can also be prepared by reacting alkylphenols with elemental sulfur. Also suitable as detergents are neutral and basic salts of phenols, generally known as phenates, wherein the phenol is generally an alkyl substituted phenolic group, where the substituent is an aliphatic hydrocarbon group having about 4 to 400 carbon atoms.

Some organometallic compounds, for example, barium organometallics, act as combustion catalysts, and can be used as smoke suppressants. Adding these compounds to fuel can reduce the black smoke emissions that result from incomplete combustion. Smoke suppressants based on other metals, e.g., iron, cerium, or platinum can also be used.

Anti-foaming additives such as organosilicone compounds can be used, typically at concentrations of 10 ppm or less. Examples of anti-foaming agents include polysiloxanes such as silicone oil and polydimethyl siloxane; acrylate polymers are also suitable.

Antioxidants can be added to the fuel or fuel additive composition to neutralize or minimize degradation chemistry. Suitable antioxidants include, for example, hindered phenols and certain amines, such as phenylenediamine. They are typically used in the concentration range of 10 ppm to 80 ppm. Examples of antioxidants include those described in U.S. Pat. No. 5,200,101, which discloses certain amine/hindered phenol, acid anhydride and thiol ester-derived products.

Multi-component fuel stabilizer packages may contain a dispersant. Dispersants are typically used in the concentration range of 15 ppm to 100 ppm.

Examples of friction modifiers include fatty acid esters and amides, glycerol esters of dimerized fatty acids and succinate esters or metal salts thereof.

Examples of anti-wear agents include zinc dialkyldithiophosphate, zinc diary diphosphate, and sulfurized isobutylene. Additional additives are described in U.S. Pat. No. 5,898,023 to Francisco et al., the contents of which are hereby incorporated by reference.

VIII. Methods for Converting Lignin to Hydrocarbons

As discussed above, the use of lignocellulosic materials provides, in addition to the fermentable sugars, a significant amount of lignin. The lignin can simply be burned, and the thermal energy used to provide energy for other steps described elsewhere herein. The lignin can also be converted to electric power, for example, when its heat energy is passed through a steam turbine to generate electricity. This electricity can be used to power the Kolbe electrolysis step.

The lignin can also be converted to synthesis gas, and the synthesis gas used to generate alcohols, such as methanol or ethanol, or hydrocarbons. The hydrocarbons can be converted, using known steps, to jet fuel, diesel fuel, and/or gasoline, among other products. The conversion to synthesis gas is typically carried out at high temperatures, often using "black liquor" resulting from the delignification of lignocellulosic materials. The black liquor includes inorganic pulping chemicals and lignin, among other substances. At high temperatures, a complex gas mixture including primarily carbon monoxide, hydrogen, carbon dioxide and methane is produced, and the inorganic chemicals can be isolated and reused, for example, in pulping operations. Because of its relatively high sulfur content, this gas mixture must be desulfurized before use in Fischer-Tropsch synthesis. Fischer-Tropsch synthesis is are well known to those of skill in the art, and thus not described in detail here.

IX. Use of the Process in Combination with Algae to Form Triglycerides/Biodiesel In a separate embodiment, the carbon dioxide produced during the fermentation and/or the Kolbe electrolysis steps can be used to grow algae, ideally strains of algae which produce relatively high volumes of triglycerides (i.e., greater than 30% by weight). The triglycerides can optionally be extracted using the hexane or hexane isomers produced using the process described herein.

X. Use of the Hydrogen Formed During the Fermentation and Kolbe Steps

At least a portion of the hydrogen formed during the fermentation and/or Kolbe electrolysis can be isolated, and used in hydrogenation reactions, fuel cells, Fischer-Tropsch synthesis, hydrocracking, or other such uses for hydrogen, as are known in the art.

All references cited herein are hereby incorporated by reference in their entirety, for all purposes. Modifications and variations of the present invention relating to a fuel additive composition and an alternative fuel derived from the composition will be obvious to those skilled in the art from the foregoing detailed description of the invention.

The invention claimed is:

1. A method for preparing hexane, comprising the steps of: a) subjecting an aqueous solution comprising glucose, xylose, sucrose, and/or fructose to fermentation conditions using a yeast or bacteria which produces, as a fermentation product, predominantly butyric acid and carbon dioxide, b) subjecting the butyric acid to Kolbe electrolysis and/or photo-Kolbe electrolysis to form a product mixture comprising hexane, and c) isolating the hexane.

2. The method of claim 1, wherein the aqueous solution comprising glucose, xylose and/or fructose is obtained from a lignocellulosic material by steps comprising: a) delignification, and b) depolymerization of cellulose and/or hemicellulose.

3. The method of claim 1, wherein the source of the glucose, xylose, and/or fructose comprises corn syrup or other steepwater.

4. The method of claim 1, wherein the source of the glucose, xylose, and/or fructose comprises switchgrass or sugar cane bagasse.

5. The method of claim 1, wherein the source of the glucose, xylose, and/or fructose comprises wood, sawdust, wood chips, pulp, and/or paper.

6. The method of claim 1, wherein the source of the glucose, xylose, and/or fructose is derived from corn.

7. The method of claim 1, wherein the bacteria is *Clostridium tyrobutyricum*, which are which has been genetically modified to produce less acetic acid than the wild-type bacteria.

8. The method of claim 1, wherein the hexane is further subjected to catalytic reforming and/or isomerization to form gasoline or components of a gasoline composition.

9. The method of claim 2, further comprising isolating lignin during the delignification process and converting the lignin to synthesis gas.

10. The method of claim 9, wherein the synthesis gas is subjected to Fisher-Tropsch synthesis.

11. The method of claim 1, wherein the carbon dioxide produced during the fermentation and/or Kolbe electrolysis steps is sequestered with algae.

12. The method of claim 11, wherein the algae generate triglycerides.

13. The method of claim 12, wherein the triglycerides are extracted from the algae using at least a portion of the hexane produced in the process of claim 1.

* * * * *